(12) United States Patent
Luyken et al.

(10) Patent No.: US 6,346,641 B1
(45) Date of Patent: Feb. 12, 2002

(54) METHOD FOR SIMULTANEOUS PRODUCTION OF 6-AMINOCAPRONITRILE AND HEXAMETHYLENEDIAMINE

(75) Inventors: Hermann Luyken, Ludwigshafen; Frank Ohlbach, Dossenheim; Andreas Ansmann, Wiesloch; Peter Bassler, Viernheim; Rolf Fischer, Heidelberg; Johann-Peter Melder, Böhl-Iggelheim; Martin Merger, Frankenthal; Alwin Rehfinger, Mutterstadt; Guido Voit, Freinsheim; Günther Achhammer, Mannheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/720,882

(22) PCT Filed: Jul. 2, 1999

(86) PCT No.: PCT/EP99/04583
§ 371 Date: Jan. 2, 2001
§ 102(e) Date: Jan. 2, 2001

(87) PCT Pub. No.: WO00/05191
PCT Pub. Date: Feb. 3, 2000

(30) Foreign Application Priority Data
Jul. 20, 1998 (DE) ......... 198 32 590

(51) Int. Cl.$^7$ .................... C07C 255/00
(52) U.S. Cl. ................... 558/459
(58) Field of Search ............. 558/459

(56) References Cited

U.S. PATENT DOCUMENTS

| | | |
|---|---|---|
| 3,322,815 A | 5/1967 | Feldman |
| 3,696,153 A | 10/1972 | Kershaw |
| 4,601,859 A | 7/1986 | Galle |
| 5,527,946 A | 6/1996 | Flick |
| 5,646,277 A | 7/1997 | Fuchs |
| 6,147,247 A | * 11/2000 | Voit et al. ............ 558/459 |

FOREIGN PATENT DOCUMENTS

| | | |
|---|---|---|
| DE | 848 654 | 9/1952 |
| DE | 954 416 | 12/1956 |
| DE | 42 35 466 | 4/1994 |
| DE | 195 48289 | 6/1997 |
| DE | 196 36766 | 3/1998 |
| DE | 196 36767 | 3/1998 |
| WO | 96/18603 | 6/1996 |
| WO | 96/20166 | 7/1996 |
| WO | 96/23802 | 8/1996 |
| WO | 96/23804 | 8/1996 |
| WO | 97/10052 | 3/1997 |

* cited by examiner

Primary Examiner—Joseph K. McKane
Assistant Examiner—Joseph Murray
(74) Attorney, Agent, or Firm—Keil & Weinkauf

(57) ABSTRACT

A process for the coproduction of 6-aminocapronitrile and hexamethylenediamine starting from adiponitrile by a) hydrogenating adiponitrile in the presence of a catalyst comprising an element of the eighth transition group as catalytically active component, to obtain a mixture comprising 6-aminocapronitrile, hexamethylenediamine, adiponitrile and high boilers, b) distillatively removing hexamethylenediamine from the mixture comprising 6-aminocapronitrile, hexamethylenediamine, adiponitrile and high boilers, and either c1) distillatively removing 6-aminocapronitrile, and then d1) distillatively removing adiponitrile, or c2) simultaneously distillatively removing 6-aminocapronitrile and adiponitrile into separate fractions is characterized by base of column temperatures below 185° C. in steps d1) or c2).

16 Claims, 1 Drawing Sheet

Figure 1:
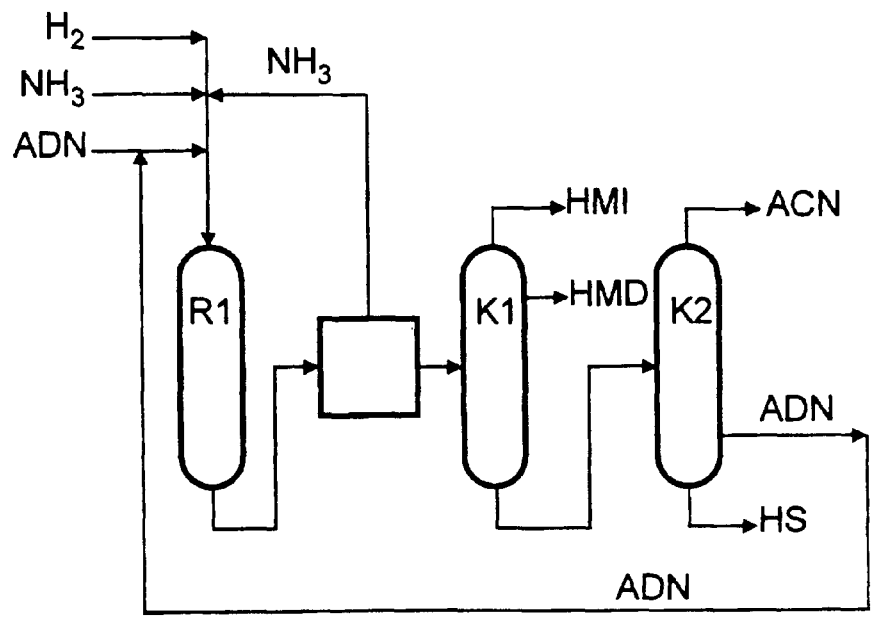

METHOD FOR SIMULTANEOUS PRODUCTION OF 6-AMINOCAPRONITRILE AND HEXAMETHYLENEDIAMINE

This application is a 371 of PCT/EP99/04583 filed Jul. 2, 1999.

The present invention relates to a process for the coproduction of 6-aminocapronitrile and hexamethylenediamine starting from adiponitrile by a) hydrogenating adiponitrile in the presence of a catalyst comprising an element of the eighth transition group as catalytically active component, to obtain a mixture comprising 6-aminocapronitrile, hexamethylenediamine, adiponitrile and high boilers, b) distillatively removing hexamethylenediamine from the mixture comprising 6-aminocapronitrile, hexamethylenediamine, adiponitrile and high boilers, and either c1) distillatively removing 6-aminocapronitrile, and then d1) distillatively removing adiponitrile, or c2) simultaneously distillatively removing 6-aminocapronitrile and adiponitrile into separate fractions, characterized by base of column temperatures below 185° C. in steps d1) or c2).

It is known to hydrogenate adiponitrile in the presence of elements of the eighth transition group, especially in the presence of predominantly iron, cobalt, nickel, ruthenium or rhodium catalysts, solvents such as, for example, ammonia, amines or alcohols, and optionally additives such as, for example, inorganic bases to obtain mixtures comprising 6-aminocapronitrile, hexamethylenediamine and unconverted adiponitrile. The catalysts used are catalysts homogeneously dissolved in the liquid phase or fixed bed catalysts used as fixed bed or in suspension.

Iron catalysts, which are generally used as fixed bed catalysts in the liquid phase at high pressure, are described for example in DE 4235466, WO 96/20166, WO 96/20043 and DE 19636767. Cocatalysts are known for example from DE 954416, WO 96/20166 and DE 19636768. Nickel catalysts are used according to DE 848654 for example as supported catalysts (nickel on $Al_2O_3$), but in particular according for example to U.S. Pat. No. 2,762,835, WO 96/18603 and WO 97/10052 in the form of doped or undoped Raney nickel. Ruthenium fixed bed catalysts are known from U.S. Pat. No. 3,322,815, homogeneously dissolved ruthenium catalysts from WO 96/23802 and WO 96/23804. Rhodium catalysts, for example rhodium on magnesium oxide, are mentioned in U.S. Pat. No. 4,601,859 for example.

The partial hydrogenation of adiponitrile to form mixtures of 6-aminocapronitrile, hexamethylenediamine and unconverted adiponitrile is carried out in order that 6-aminocapronitrile and hexamethylenediamine may be obtained in a desired ratio which is adjustable through suitable choice of the reaction conditions. 6-Aminocapronitrile can be cyclized, for example according to U.S. Pat. No. 5,646,277, into caprolactam in the liquid phase in the presence of oxidic catalysts. Caprolactam is the precursor for nylon-6, and hexamethylenediamine is one of the two intermediates for manufacturing nylon-6,6.

DE-A 19548289 discloses a process for the coproduction of 6-aminocapronitrile and hexamethylenediamine by hydrogenation of adiponitrile in the presence of a catalyst to partial conversion, the removal of hexamethylenediamine and 6-aminocapronitrile from the mixture and conversion of 6-aminocapronitrile into caprolactam and also recycling into the process of a portion consisting essentially of adiponitrile.

The disadvantage with these processes is that the adiponitrile recovered in the course of the workup of the reaction effluent contains undesirable by-products, especially amines, such as 1-amino-2-cyanocyclopentene (ACCPE), 2-(5-cyanopentylamino)tetrahydroazepine (CPATHA) and bishexamethylentriamine (BHMTA).

According to the processes described, the by-products are impossible to separate from adiponitrile by distillation because of the formation of azeotropes or quasi-azeotropes. The result is, especially if the adiponitrile is recycled, a buildup of the by-products in the overall process.

Recycled ACCPE may become hydrogenated to 2-aminomethyl-cyclopentylamine (AMCPA), which is an impurity when the product of value is hexamethylenediamine. U.S. Pat. No. 3,696,153 discloses that AMCPA is very difficult to separate from hexamethylenediamine.

DE 19636766 discloses admixing the adiponitrile to be recycled with from 0.01 to 10% by weight of an acid, based on adiponitrile, or an acidic ion exchanger, to remove the adiponitrile from this mixture and to recycle it into the hydrogenation reactor. The addition of acid serves to neutralize nitrogenous basic by-products. The disadvantage with this method is the formation of salts, which have to be removed from the process and disposed of. This necessitates an additional process step.

It is an object of the present invention to provide a process for removing adiponitrile from an adiponitrile partial hydrogenation product mixture comprising adiponitrile, hexamethylenediamine, 6-aminocapronitrile and components having a boiling point above that of adiponitrile ("high boilers") in a technically simple and economical manner while avoiding the disadvantages mentioned and recovering very pure adiponitrile.

We have found that this object is achieved by the process defined at the beginning.

The partial hydrogenation of adiponitrile can be carried out according to one of the known processes, for example according to one of the aforementioned processes described in 46018591, U.S. Pat. Nos. 2,762,835, 2,208,598, DE-A 848654, DE-A 9544161, WO 96/18603, WO 97/10052, DE-A 4235466 or WO 92/21650, by, in general, performing the hydrogenation in the presence of an element of the eighth transition group or mixtures thereof, such as nickel, cobalt, iron, ruthenium or rhodium catalysts. The catalysts can be used as homogeneously dissolved catalysts or as suspended or fixed bed supported or solid catalysts. Examples of suitable catalyst supports are aluminum oxide, silicon dioxide, titanium dioxide, magnesium oxide, activated carbons and spinels. Examples of suitable solid catalysts are Raney nickel and Raney cobalt, which may each be doped with further metals.

The catalyst space velocity chosen is typically within the range from 0.05 to 10 kg, preferably from 0.1 to 5 kg, of adiponitrile/l of cat. x h.

The hydrogenation is generally carried out at a temperature from 20 to 220° C., preferably within the range from 50 to 150° C., and at hydrogen partial pressures from 0.1 to 40 MPa, preferably from 0.5 to 30 MPa.

The hydrogenation is preferably carried out in the presence of a solvent such as ammonia, amines or alcohols, especially ammonia. The ammonia quantity chosen is generally within the range from 0.1 to 10 kg, preferably within the range from 0.5 to 3 kg, of ammonia/kg of adiponitrile.

The molar ratio of 6-aminocapronitrile to hexamethylenediamine and hence the molar ratio of caprolactam to hexamethylenediamine can be controlled by the particular adiponitrile conversion which is chosen. Preference is given to using adiponitrile conversions within the range from 10 to 90%, preferably within the range from 30 to 80%, in order that high 6-aminocapronitrile selectivities may be obtained.

In general, the sum total of 6-aminocapronitrile and hexamethylenediamine is within the range from 95 to 99%, depending on catalyst and reaction conditions, and hexamethyleneimine is the most significant by-product in terms of volume.

The catalysts used are preferably nickel, ruthenium, rhodium, iron and cobalt compounds, preferably those of the Raney type, especially Raney nickel and Raney cobalt. The catalysts can also be used in the form of supported catalysts, in which case suitable supports include for example aluminum oxide, silicon dioxide, zinc oxide, activated carbon or titanium dioxide (S. Appl. Het. Cat., 1987, 106–122; Catalysis, Vol. 4 (1981) 1–30). Raney nickel is particularly preferred.

The nickel, ruthenium, rhodium, iron and cobalt catalysts can advantageously be modified with metals of the groups VIB (cr, Mo, W) and VIII (Fe, Ru, Os, Co (only in the case of nickel), Rh, Ir, Pd, Pt) of the periodic table of the elements. According to observations to date, for example according to DE-A 2260978; Bull. Soc. Chem. 13 (1946) 208, the use of especially modified Raney nickel catalysts, for example chromium- and/or iron-modified, leads to higher 6-aminocapronitrile selectivities.

The amount of catalyst is generally chosen so that the cobalt, ruthenium, rhodium, iron or nickel quantity is within the range from 1 to 50% by weight, preferably within the range from 5 to 20% by weight, based on the amount of dinitrile used.

The catalysts can be used as fixed bed catalysts in upflow or downflow mode or as suspension catalysts.

In a further preferred embodiment, adiponitrile is partially hydrogenated to 6-aminocapronitrile at elevated temperature and elevated pressure in the presence of a solvent and of a catalyst by using a catalyst comprising i) a compound based on a metal selected from the group consisting of nickel, cobalt, iron, ruthenium and rhodium, ii) from 0.01 to 25% by weight, preferably from 0.1 to 5% by weight, based on a), of a promoter based on a metal selected from the group consisting of palladium, platinum, iridium, osmium, copper, silver, gold, chromium, molybdenum, tungsten, manganese, rhenium, zinc, cadmium, lead, aluminum, tin, phosphorus, arsenic, antimony, bismuth and rare earth metals, and also iii) from 0 to 5% by weight, preferably from 0.1 to 3% by weight, based on i), of a compound based on an alkali metal or an alkaline earth metal.

Preferred catalysts are those in which component i) comprises at least one compound based on a metal selected from the group consisting of nickel, cobalt and iron in an amount within the range from 10 to 95% by weight, and also ruthenium and/or rhodium in an amount within the range from 0.1 to 5% by weight, each based on the sum total of components i) to iii), component ii) comprises at least one promoter based on a metal selected from the group consisting of silver, copper, manganese, rhenium, lead and phosphorus in an amount within the range from 0.1 to 5% by weight, based on i), and component iii) comprises at least one compound based on the alkali metals and alkaline earth metals selected from the group consisting of lithium, sodium, potassium, cesium, magnesium and calcium in an amount within the range from 0.1 to 5% by weight.

Particularly preferred catalysts are those comprising i) a compound based on iron such as iron oxide, and ii) from 0 to 5% by weight based on i) of a promoter based on an element or 2, 3, 4, 5 or 6 elements selected from the group consisting of aluminum, silicon, zirconium, vanadium, manganese and titanium, and also iii) from 0 to 5% by weight, preferably from 0.1 to 3% by weight, in particular from 0.1 to 5% by weight, based on i) of a compound based on an alkali or alkaline earth metal, preferably selected from the group consisting of lithium, sodium, potassium, rubidium, cesium, magnesium and calcium.

The preferred catalysts may be solid or supported catalysts. Suitable support materials include for example porous oxides such as aluminum oxide, silicon dioxide, alumosilicates, lanthanum oxide, titanium dioxide, zirconium dioxide, magnesium oxide, zinc oxide and zeolites and also activated carbon or mixtures thereof.

They are generally prepared by precipitating precursors of components a) together with precursors of the promoters, components ii), and if desired with precursors of components iii) in the presence or absence of support materials (depending on which type of catalyst is desired), if desired processing the resulting catalyst precursor into extrudates or tablets, drying and subsequently calcining. Supported catalysts are generally also obtainable by saturating the support with a solution of components i), ii) and if desired iii), the individual components being added simultaneously or in succession, or by spraying the components i), ii) and if desired iii) onto the support in a conventional manner.

Suitable precursors for components i) generally include readily water-soluble salts of the aforementioned metals such as nitrates, chlorides, acetates, formates and sulfates, preferably nitrates. Suitable precursors for component ii) generally include readily water-soluble salts or complexes of the aforementioned metals such as nitrates, chlorides, acetates, formates and sulfates and also especially hexachloroplatinate, preferably nitrates and hexachloroplatinate.

Suitable precursors for components iii) generally include readily water-soluble salts of the aforementioned alkali metals and alkaline earth metals such as hydroxides, carbonates, nitrates, chlorides, acetates, formates and sulfates, preferably hydroxides and carbonates.

They are generally precipitated from aqueous solutions, selectively by addition of precipitants, by changing the pH or by changing the temperature.

The catalyst prematerial thus obtained is usually dried, generally at from 80 to 150° C., preferably at from 80 to 120° C. Calcination is customarily carried out at from 150 to 500° C., preferably at from 200 to 450° C., in a gas stream comprising air or nitrogen.

After calcination, the catalyst material obtained is generally activated by exposing it to a reducing atmosphere, for example by exposing it for from 2 to 24 hours to a hydrogen atmosphere or to a gas mixture comprising hydrogen and an inert gas, such as nitrogen, at from 80 to 250° C., preferably at from 80 to 180° C., in the case of catalysts based on ruthenium and rhodium as components i), or at from 200 to 500° C., preferably at from 250 to 400° C., in the case of catalysts based on one of the metals selected from the group consisting of nickel, cobalt and iron as component I). The catalyst space velocity here is preferably 200 l/l of catalyst.

Advantageously, the activation of the catalyst is carried out directly in the synthesis reactor, since this customarily dispenses with an otherwise necessary intermediary step, i.e., the passivation of the surface, customarily at from 20 to 80° C., preferably at from 25 to 35° C., by means of oxygen/nitrogen mixtures such as air. The activation of passivated catalysts is then preferably carried out in the synthesis reactor at from 180 to 500° C., preferably at from 200 to 350° C., in an atmosphere comprising hydrogen.

The catalysts may be used in a reactor R1 as fixed bed catalysts in upflow or downflow mode or as suspension catalysts (see FIG. 1).

If the reaction is carried out in a suspension, it is customary to choose temperatures within the range from 40 to 150° C., preferably within the range from 50 to 100° C., particularly preferably within the range from 60 to 90° C.; the pressure is generally chosen within the range from 2 to 30 MPa, preferably within the range from 3 to 30 MPa, particularly preferably within the range from 4 to 9 MPa. The residence times are essentially dependent on the desired yield, selectivity and the desired conversion; the residence time is customarily chosen so as to maximize the yield, for example within the range from 50 to 275 minutes, preferably within the range from 70 to 200 minutes.

In the suspension procedure, it is advantageously possible to use in particular liquid diluents, advantageously primary, secondary or tertiary amines, such as monoamines, diamines and triamines having from 1 to 6 carbon atoms, for example trimethylamine, triethylamine, tripropylamine and tributylamine, or alcohols, especially methanol and ethanol, preferably ammonia, or mixtures thereof. It is advantageous to choose an adiponitrile concentration within the range from 10 to 90% by weight, preferably within the range from 30 to 80% by weight, particularly preferably within the range from 40 to 70% by weight, based on the sum total of adiponitrile and diluent.

The amount of catalyst is generally chosen so that the catalyst quantity is within the range from 1 to 50% by weight, preferably within the range from 5 to 20% by weight, based on the amount of adiponitrile used.

The partial hydrogenation can also be carried out batchwise or continuously over a fixed bed catalyst in the downflow or upflow mode, in which case it is customary to choose a temperature within the range from 20 to 150° C., preferably within the range from 30 to 90° C., and a pressure which is generally within the range from 2 to 40 MPa, preferably within the range from 3 to 30 MPa.

It is advantageously possible to use in particular liquid diluents, advantageously primary, secondary or tertiary amines, such as monoamines, diamines and triamines having from 1 to 6 carbon atoms, for example trimethylamine, triethylamine, tripropylamine and tributylamine, or alcohols, especially methanol and ethanol, preferably ammonia, or mixtures thereof.

In a preferred embodiment, ammonia is used within the range from 1 to 10 g, preferably from 2 to 6 g, per g of adiponitrile. It is preferable to employ for this a catalyst space velocity within the range from 0.1 to 2.0 kg, preferably within the range from 0.3 to 1.0 kg, of adiponitrile/l x h. Here, too, the conversion and hence the selectivity can be controlled by changing the residence time.

It is advantageous to add basic additives, especially hydroxides, carbonates or alkoxides of alkali or alkaline earth metals or mixtures of such compounds, in the hydrogenation of step a).

If a diluent was added in step a), it may advantageously be removed between step a) and step b) in a conventional manner, preferably by distillation, and be reused, for example in step a).

Figure 2:
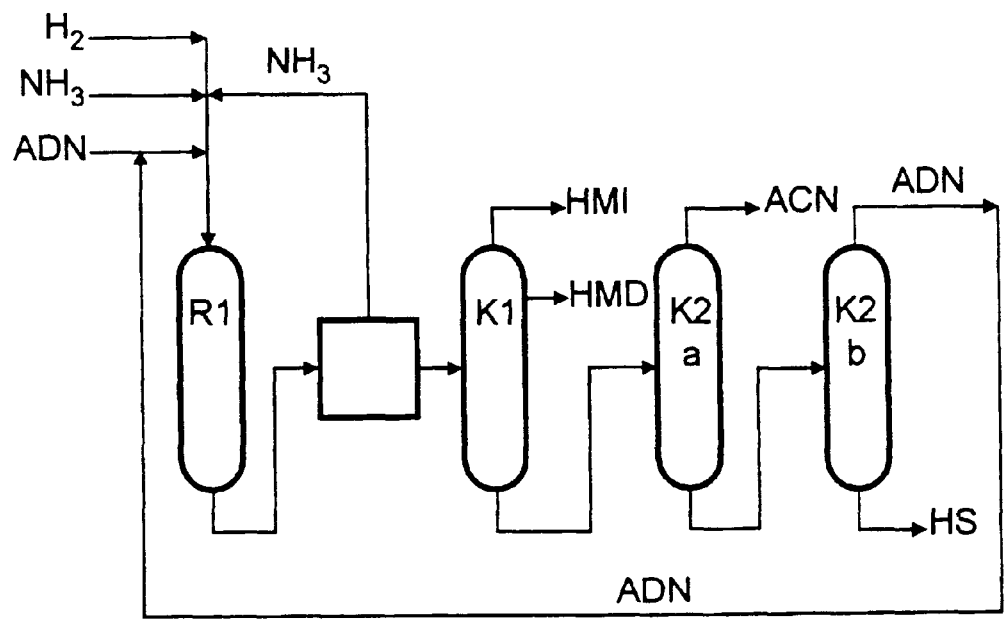

The hydrogenation effluent of the present invention can be worked up in two sequences of steps (see FIGS. 1 and 2).

The reaction effluent initially has hexamethylenediamine removed from it together with the by-product hexamethyleneimine (step b)). This can take place in two or more columns, preferably one column (K 1).

In a preferred embodiment, the base of column temperature in step b) should be below 185° C., preferably below 180° C., but the low vapor pressure of the compounds to be separated means that the base of column temperature should not be less than 100° C., preferably not less than 130° C. The pressures at the base of the column should advantageously be within the range from 0.1 to 100, especially from 5 to 40, mbar. The residence times of the bottom product in the distillation of step b) should preferably be within the range from 1 to 60, especially 5 to 15, minutes.

The bottom product obtained from the distillation of step b) can be worked up in two alternative ways, step sequence c1) and d1) or step c2).

According to step c2 (FIG. 1), the bottom product is fed into a column K 2, where 6-aminocapronitrile is removed overhead, adiponitrile is removed in a sidestream takeoff and high boilers (HS) are removed via the bottom product.

The base of column temperature in step c2) of the present invention is below 185° C., preferably below 180° C., but the low vapor pressure of the compounds to be separated means that the base of column temperature should not be less than 100° C., preferably not less than 130° C. The pressures at the base of the tetrahydroazepine column should advantageously be within the range from 0.1 to 100, especially from 5 to 40, mbar. The residence times of the bottom product in the distillation of step c2) should preferably be within the range from 1 to 60, especially 5 to 15, minutes.

In step sequence c1)/d1) (FIG. 2), the bottom product is fed into a column K 2a, in which the 6-aminocapronitrile is distillatively removed overhead (step c1)), the bottom product is fed into a column K 2b, where adiponitrile is removed distillatively overhead (step d1)) and high boilers (HS) are removed via the bottom product.

In a preferred embodiment, the base of column temperature in step c1) should be below 185° C., preferably below 180° C., but the low vapor pressure of the compounds to be separated means that the base of column temperature should not be less than 100° C., preferably not less than 130° C. The pressures at the base of the column should advantageously be within the range from 0.1 to 100, especially from 5 to 40, mbar. The residence times of the bottom product in the distillation of step c1) should preferably be within the range from 1 to 60, especially 5 to 15, minutes.

The base of column temperature in step d1) of the present invention is below 185° C., preferably below 180° C., but the low vapor pressure of the compounds to be separated means that the base of column temperature should not be less than 100° C., preferably not less than 130° C. The pressures at the base of the column should advantageously be within the range from 0.1 to 100, especially from 5 to 40, mbar. The residence times of the bottom product in the distillation of step d1) should preferably be within the range from 1 to 60, especially 5 to 15, minutes.

To further reduce the level of by-products in the recovered adiponitrile, the process of the present invention makes it advantageously possible to feed an organic or inorganic acid batchwise or preferably continuously into the bottom region of the column K 2b or for the adiponitrile obtained downstream of columns K 2 or K 2b to be purified, batchwise or preferably continuously, with an organic or inorganic acid.

The adiponitrile obtained by either alternative may advantageously be used in the partial hydrogenation to form 6-aminocapronitrile and hexamethylenediamine, for example by recycling into step a) of the process of the invention, or into a process for complete hydrogenation to hexamethylenediamine.

Surprisingly, recycling the adiponitrile recovered by the process of the present invention into the partial hydrogenation process was found to lead to considerable advantages in the hydrogenation, the distillative purification of hexamethylenediamine and the onstream time of the hydrogenation catalyst because the present invention has reduced the level of 1-amino-2-cyanocyclopentene in the recycled adiponitrile.

EXAMPLE 1 a) Preparation of an Iron Hydrogenation Catalyst

The partial hydrogenation of adiponitrile to 6-aminocapronitrile and hexamethylenediamine was carried out using an iron catalyst which was based on a magnetite ore and prepared according to Example 2 a) of DE 19636767. The particle size fraction used ranged from 3 to 5 mm.

b) Partial Hydrogenation of Adiponitrile

A tubular reactor (180 cm in length and 30 mm in internal diameter) was packed with 720 ml (1630 g) of the catalyst material prepared according to a) and reduced in a 500 standard l/h hydrogen stream under atmospheric pressure. The temperature was raised from 30° C. to 340° C. over 24 hours and then maintained at 340° C. for 72 hours.

After the temperature was lowered, the reactor was fed at 250 bar and 90° C. feed temperature with 330 g/h of ADN, 1200 g/h of ammonia and 140 standard l/h of hydrogen.

The hydrogenation was operated for 1500 hours under the stated conditions. Throughout the entire duration of the run, an ADN conversion of 60% gave a constant total selectivity (sum total of the selectivities of 6-aminocapronitrile and hexamethylene-diamine) of 99%. The 6-aminocapronitrile selectivity decreased from 50% to 48.5% in the course of the run.

c) Workup of Hydrogenation Effluent

Hydrogenation effluents were collected during the run for the workup, which was carried out batchwise.

First, ammonia was distilled out of the effluents overhead in a column having 20 theoretical plates. The bottom product obtained was a mixture which, according to analysis by gas chromatography, was 30 mol % 6-aminocapronitrile, 39 mol % adiponitrile and 30 mol % hexamethylenediamine. The most significant by-product by volume was hexamethyleneimine.

On processing 1000 g of the bottom product in the same column, 296 g of hexamethylenediamine were removed overhead at a base of column temperature of 180° C. and found to contain about 0.5% by weight of hexamethyleneimine.

695 g of the bottom product obtained were distilled in a continuously operated column in such a way as to remove around 305 g of 6-aminocapronitrile overhead, 380 g of adiponitrile via a sidestream takeoff and 10 g of adiponitrile-comprising high boilers as bottom product. The distillation was carried out at a top of column pressure of from 20 to 40 mbar.

The base of column temperature was varied by varying the top of column pressure. The reflux ratio was 2:1. Table 1 shows the dependence of the 1-amino-2-cyanocyclopentene quantity in the adiponitrile of the sidestream takeoff as a function of the base of column temperature.

TABLE 1

| Base of column temperature (° C.) | ACCPE[1] (ppm) |
|---|---|
| 198.5 | 12300 |
| 184.9 | 11300 |
| 184.2 | 8900 |
| 182.2 | 3600 |
| 182.0 | 3200 |
| 180.9 | 2700 |
| 180.5 | 2700 |
| 180.0 | 2800 |
| 178.2 | 2800 |

[1]ppm of 1-amino-2-cyanocyclopentene based on adiponitrile obtained in a sidestream takeoff

We claim:
1. The process for the coproduction of 6-aminocapronitrile and hexamethylenediamine starting from adiponitrile, which comprises the steps of
   a) hydrogenating adiponitrile in the presence of a catalyst comprising an element of the eighth transition group as catalytically active component, to obtain a mixture comprising 6-aminocapronitrile, hexamethylenediamine, adiponitrile and high boilers,
   b) distillatively removing hexamethylenediamine from the mixture comprising 6-aminocapronitrile, hexamethylenediamine, adiponitrile and high boilers, and either
   c1) distillatively removing 6-aminocapronitrile, and then
   d1) distillatively removing adiponitrile, or
   c2) simultaneously distillatively removing 6-aminocapronitrile and adiponitrile into separate fractions,
characterized by base of column temperatures below 185° C. in steps d1) or c2).

2. The process as claimed in claim 1, wherein base of column temperatures are below 180° C. in steps d1) or c2).

3. The process as claimed in claim 1, wherein the catalyst in step a) comprises iron, cobalt, nickel, ruthenium or rhodium or mixtures thereof as catalytically active element.

4. The process as claimed in claim 1, wherein the catalyst in step a) comprises iron, cobalt or nickel or mixtures thereof as catalytically active element.

5. The process as claimed in claim 1, wherein the catalyst in step a) is based on Raney nickel or Raney cobalt or mixtures thereof.

6. The process as claimed in claim 1, wherein the catalyst used in step a) comprises
   i) a compound based on a metal selected from the group consisting of nickel, cobalt, iron, ruthenium and rhodium,
   ii) from 0.01 to 25% by weight, based on I), of a promoter based on a metal selected from the group consisting of palladium, platinum, iridium, osmium, copper, silver, gold, chromium, molybdenum, tungsten, manganese, rhenium, zinc, cadmium, lead, aluminum, tin, phosphorus, arsenic, antimony, bismuth and rare earth metals, and also
   iii) from 0 to 5% by weight, based on i), of a compound based on an alkali metal or an alkaline earth metal.

7. The process as claimed in claim 1, wherein the catalyst used in step a) comprises
   i) a compound based on iron,
   ii) from 0 to 5% by weight based on i) of a promoter based on an element or 2, 3, 4, 5 or 6 elements selected from the group consisting of aluminum, silicon, zirconium, manganese, vanadium and titanium, and also iii) from 0 to 5% by weight based on i) of a compound based on an alkali or alkaline earth metal.

8. The process as claimed in claim 1, wherein a diluent is additionally used in step a).

9. The process as claimed in claim 8, wherein the diluent used is selected from primary, secondary or tertiary amines, ammonia or alcohols or mixtures thereof.

10. The process as claimed in claim 8, wherein the diluent is removed between steps a) and b).

11. The A process as claimed in claim 1, wherein basic substances are additionally added in step a).

12. The process as claimed in claim 11, wherein the basic substances used are hydroxides, carbonates or alkoxides of the alkali or alkaline earth metals or mixtures thereof.

13. The process as claimed in claim 1, wherein adiponitrile is recycled into step a) after steps d1) or c2).

14. The process as claimed in claim 13, wherein the adiponitrile recycled into step a) is hydrogenated to hexamethylenediamine after steps d1) or c2).

15. The process as claimed in claim 6, wherein the catalyst promoter element of ii) is present in the amount of from 0.1 to 5% by weight, based on I).

16. The process as claimed in claim 6, wherein the alkali metal or alkaline earth metal of iii) is present in the amount of from 0.1 to 3% by weight, based on I).

* * * * *